US009867686B2

(12) United States Patent
Soares Da Costa et al.

(10) Patent No.: US 9,867,686 B2
(45) Date of Patent: Jan. 16, 2018

(54) IMPLANTABLE HERNIA PROSTHESIS WITH AN UNINTERRUPTED RING

(71) Applicant: Bard Shannon Limited, Humacao, PR (US)

(72) Inventors: Rui Manuel De Melo Soares Da Costa, Oporto (PT); Augusto Manuel De Almeida Lourenço, Guarda (PT)

(73) Assignee: Bard Shannon Limited, Humacao, PR (US)

( * ) Notice: Subject to any disclaimer, the term of this patent is extended or adjusted under 35 U.S.C. 154(b) by 0 days.

(21) Appl. No.: 14/347,175

(22) PCT Filed: Sep. 25, 2012

(86) PCT No.: PCT/PT2012/000038
§ 371 (c)(1),
(2) Date: Mar. 25, 2014

(87) PCT Pub. No.: WO2013/048272
PCT Pub. Date: Apr. 4, 2013

(65) Prior Publication Data
US 2014/0379007 A1    Dec. 25, 2014

(30) Foreign Application Priority Data
Sep. 26, 2011 (PT) .......................................... 105907

(51) Int. Cl.
*A61F 2/02* (2006.01)
*A61F 2/00* (2006.01)

(52) U.S. Cl.
CPC .... *A61F 2/0063* (2013.01); *A61F 2230/0015* (2013.01); *A61F 2250/0031* (2013.01)

(58) Field of Classification Search
CPC ............ A61F 2/0063; A61F 2230/0015; A61F 2250/0031; A61F 2002/0068; A61F 2002/0072

USPC ........................................ 623/23.72; 606/151
See application file for complete search history.

(56) References Cited

U.S. PATENT DOCUMENTS

| 5,716,409 | A |   | 2/1998 | Debbas |
| 5,769,864 | A |   | 6/1998 | Kugel |
| 5,824,082 | A | * | 10/1998 | Brown .................. A61F 2/0063 623/11.11 |
| 5,916,225 | A |   | 6/1999 | Kugel |
| 5,954,767 | A |   | 9/1999 | Pajotin et al. |
| 6,166,286 | A |   | 12/2000 | Trabucco |
| 6,171,318 | B1 |   | 1/2001 | Kugel et al. |
| 6,174,320 | B1 |   | 1/2001 | Kugel et al. |

(Continued)

FOREIGN PATENT DOCUMENTS

WO    WO 06/053291 A2    5/2006

OTHER PUBLICATIONS

International Preliminary Report on Patentability, PCT/PT2012/00038, dated Apr. 1, 2014, 5 pgs.

*Primary Examiner* — Diane Yabut
*Assistant Examiner* — Martin T Ton
(74) *Attorney, Agent, or Firm* — Wolf, Greenfield & Sacks, P.C.

(57) ABSTRACT

The implantable hernia prosthesis of the present invention comprises at least one piece of mesh (1) arranged to cover at least a portion of the hernia, at least one support element (2) attached to said piece of mesh (1), said support element (2) comprising at least one resilient, deformable biasing filament, characterized by said support element (2) being an uninterrupted tension providing ring surrounding a portion of said mesh (1) and further comprising an indentation directed towards the center of said ring.

14 Claims, 3 Drawing Sheets

(56) References Cited

U.S. PATENT DOCUMENTS

| | | | |
|---|---|---|---|
| 6,214,020 B1 | 4/2001 | Mulhauser et al. | |
| 6,224,616 B1 | 5/2001 | Kugel | |
| 6,258,124 B1 | 7/2001 | Darois et al. | |
| 6,280,453 B1 | 8/2001 | Kugel et al. | |
| 6,290,708 B1 | 9/2001 | Kugel et al. | |
| 6,497,650 B1 | 12/2002 | Nicolo | |
| 6,565,580 B1 | 5/2003 | Beretta | |
| 6,652,595 B1 | 11/2003 | Nicolo | |
| 6,669,735 B1 | 12/2003 | Pelissier | |
| 6,723,133 B1 | 4/2004 | Pajotin | |
| 6,736,823 B2 | 5/2004 | Darois et al. | |
| 6,740,122 B1 | 5/2004 | Pajotin | |
| 6,790,213 B2 | 9/2004 | Cherok et al. | |
| 7,156,804 B2 | 1/2007 | Nicolo | |
| 7,404,819 B1 | 7/2008 | Darois et al. | |
| 7,824,420 B2 | 11/2010 | Eldridge et al. | |
| 8,182,545 B2 | 5/2012 | Cherok et al. | |
| 2001/0049538 A1 | 12/2001 | Trabucco | |
| 2003/0078602 A1* | 4/2003 | Rousseau | A61F 2/0063 606/151 |
| 2004/0073257 A1 | 4/2004 | Spitz | |
| 2004/0181288 A1 | 9/2004 | Darois et al. | |
| 2005/0159777 A1 | 7/2005 | Spitz | |
| 2006/0064175 A1* | 3/2006 | Pelissier | A61F 2/0063 623/23.72 |
| 2007/0032881 A1 | 2/2007 | Browning | |
| 2007/0225804 A1 | 7/2007 | Checa Ayet | |
| 2011/0015760 A1* | 1/2011 | Kullas | A61F 2/0063 623/23.72 |
| 2011/0208217 A1 | 8/2011 | Checa Ayet | |
| 2012/0078274 A1 | 3/2012 | Nicolo | |

\* cited by examiner

IMPLANTABLE HERNIA PROSTHESIS WITH AN UNINTERRUPTED RING

TECHNICAL FIELD

The present invention is related to an implantable prosthesis suitable for use in the correction and repair of hernias (indirect and direct inguinal or femoral hernias) without the need of fixing the prosthesis to any part of the body.

BACKGROUND ART

For several decades, the preferred method of treating anatomical defects has been through the use of prosthetic materials of varied shapes and features. They are typically put and fixed into place by means of sutures, staples, tackers, biological glues or simply anchored on top of, below or on the defect. Tissue growth through the prosthetic mesh, which results from the body's reaction to a foreign object, then completes the repair.

In the specific case of inguinal hernias, the prosthesis typically consists of a mesh which is woven as a net of a specific fiber. Said prosthesis is put in the location to be treated and may then be cut and/or adjusted if necessary, so that its shape and size are perfectly adapted to the inguinal area where it will be implanted.

In patients of the male sex, so as to accommodate the spermatic cord, it is normally necessary to cut the prosthesis into two separate yet still attached leafs and then adapt them to the area so as to allow for the passage of said cord and the reinforcement of the internal inguinal ring. There are already today meshes that have these areas pre-cut and others which have the areas to be cut in surgery pre-defined on the prosthesis.

Patent document no. WO2006/034117 describes various embodiments of an implantable prosthesis which are similar to the present invention. The preferred embodiment described in patent document no. WO2006/034117 is a non-absorbable, ellipsoid and symmetric along its longest axis, implantable prosthesis with a non-continuous and non-absorbable ring which substantially follows the external border of the mesh with the exception of an indentation aimed at protecting the femoral vessels, said ring being attached by means of stitching on both sides of the ring all along its length, there being two reinforcements around the edges of the ring where it is discontinued so that these do not protrude out of the channel created by said sewing of the two layers of mesh. The implantable prosthesis described in patent document no. WO2006/034117 seems to have been designed in that way (i.e, having a discontinuous ring) so as to allow for the passage of the spermatic cord through the prosthesis during the treatment of indirect inguinal hernias.

The inventors of the present invention have determined that the surgery techniques for the treatment of inguinal hernias of the prior art are not the most suitable. Indeed, several advantages can be obtained if one opts for a new surgical technique developed by the inventors of the present invention and which consists of making a much higher entry incision, thus allowing for a much better access to the ideal location for placing prostheses of the abdominal wall and to the structures, as well as enabling an easier dissection of these, a large reduction of the risk of nerve damage, less aggressive impact and a reduction in post-operatory pain, as well as a significant reduction of the time of operation. The technique of this procedure involves a 3-4 cm transversal incision in the skin two fingers above the pubic symphysis, followed by a transversal incision of the external oblique aponeurosis (the only structure that is cut in the procedure) and a broad dissection of the pre-peritoneal area (Retzius space), the isolation of the structures of the spermatic cord, the identification of the Cooper ligament and the disruption of the Fascia Transversalis at that level. After this, one proceeds with the placement of a prosthesis (e.g., a preformed mesh with a memory ring) in the various locations of existing or potential defects and, after verifying a correct haemostasis, the surgeon sutures the external oblique aponeurosis and closes up the surgical intervention. As mentioned above, the prostheses currently known and used in the prior art are not suitable, namely because the rings have discontinuations (breaks) in them or it is necessary to make such discontinuations during surgery, particularly when operating on male patients.

A continuous ring increases the memory effect, as well as a more medial placement does not interfere with the sub-aponeurotic placement of the external part of the prosthesis, which enables a better adjustment to the new surgical technique described above that is used by the inventors, as well as a reduction of some complications resulting from the format of the prosthesis ring shown in document WO2006/034117.

The new surgical technique developed by the inventors, which is not yet part of the state of the art because it has not been publically disclosed, can not only be optimized with the prosthesis of the present invention but also vice-versa.

DISCLOSURE OF INVENTION

The present invention consists of an implantable prosthesis for the repair and prevention of hernias (indirect and direct inguinal or femoral hernias).

Said implantable prosthesis comprises at least one piece of mesh attached to at least one support element which serves to provide said piece of mesh with resilience/memory properties. The resilience/memory (biasing) properties enable the implantable prosthesis to be deformed and then return to its initial shape and thus maintain the piece of mesh connected to the support element stretched.

Said support element may be connected to the piece of mesh by several alternative fixing means, provided that they do not affect the health of the patient or the ability to perform the surgery. The fixing means that are currently considered most suitable include gluing with specific glues, vulcanization, adhesiveness, impregnation or sewing.

The piece of mesh is shaped in the format of a deformed water drop, with one of the extremities being wider then the opposing extremity. The main surface area of the piece of mesh shaped like a deformed water drop borders the wider extremity and is essentially ellipsoid.

The purpose of said main surface area of the piece of mesh shaped like a deformed water drop is to cover at least part of an aperture or defect in the muscle wall (i.e., hernia) of the patient.

The wider extremity of the piece of mesh (1) has an internal angle larger than the external angle of the narrower extremity, and the internal border of the narrower extremity and external border of the wider extremity have different convexities. In other words, the wider extremity is generally obtuse and the narrower extremity is acute.

In a specific embodiment of the invention, it is also foreseen that the piece of mesh also have a cephalic axial extension, which serves to be placed over possible apertures or defects of the muscle wall above the inguinal floor. Aside from this cephalic axial extension, said piece of mesh has another laterocaudal extension, the purpose of which is to be placed over crural hernias and therefore prevent and/or correct them.

In a specific preferred embodiment, the piece of mesh (1) is asymmetric both on its major (x) and minor axis (y), and has two slight indentations, one positioned between the aforementioned cephalic axial and latero-caudal extensions and another medial in relation to the interior angle of the wider extremity.

The shape of the piece of mesh on its more medial side is also designed to prevent potential relapses in the most common location, which is the most inferior and internal and, therefore, in a preferred embodiment of the invention, said piece of mesh extends beyond the support element so that its adjustment to the location to be corrected is even better. The piece of mesh is flat and can be inverted so that it can be applied both on the right and the left sides of the patient. However, one should note that in other embodiments of the invention, the piece of mesh may adopt other shapes (e.g., concave or convex or other more complex shapes) provided that it enables a perfect adjustment to the location where it will be placed.

The piece of mesh can be made of any absorbable and/or non-absorbable woven net that allows the maintenance of the necessary properties for the correction of the herniary defect and also the maintenance of the malleability characteristics for its comfortable use, both during and after implantation. In a particularly preferred embodiment of the invention, said woven net is made of single filaments of polypropylene. As is known in the prior art, this material, when implanted, promotes rapid tissue growth through its pores and around the net of the mesh. Other materials may be used in the manufacture of the mesh such as BARD MESH® (sold by C.R. Bard, Inc.), SOFT TISSUE PATCH® (micro-porous ePTFE sold by W.L. Gore & Associates, Inc.), SURGIPRO® (sold by US Surgical, Inc.), PROLENE® e MERSILENE® (sold by Ethicon, Inc.).

As will be evident to a skilled person in the art, the size of the piece of mesh may vary and the dimensions of the prosthesis are not a fundamental aspect for the comprehension of the invention. In general, and taking into consideration the average size of the adult body of a human male and female, the size of the piece of mesh should be between 14 to 17 cm along its longest (major) axis and 8 to 10 cm along its shortest (minor) axis. In a particularly preferred embodiment of the invention, the piece of mesh should have a length of approximately 14.7 cm along its longest (major) axis and approximately 8.8 cm along its shortest (minor) axis. For embodiments of the present invention designed for the female sex or for smaller pelvises, the piece of mesh shall be approximately 16.2 cm along its longest (major) axis and approximately 9.7 cm along its shortest (minor) axis.

The support element is shaped in the form of a continuous (uninterrupted) ring. The purpose of the support element is to maintain the piece of mesh stretched, but also to provide the implantable prosthesis with properties that enable it to be deformed and then return to its initial shape. This characteristic is fundamental for the handling of the prosthesis when it implanted in the location where the hernia is to be repaired. The support element returns to its initial shape either automatically or by applying an external force. This elasticity forces the piece of mesh to remain open after it has been placed in its final destination in the patient's body.

The support element in the shape of a ring does not need to be a perfect (regular) ring. In other embodiments of the invention, the support element may be an ellipsoid ring, an ovoid ring or a geometric angled biasing structure capable of providing tension, such as, for example, a polygon with six or more sides.

The support element substantially surrounds a portion of the main surface of the piece of mesh shaped like a deformed water drop.

The support element shall have an indentation. The purpose of the indentation is to receive the inguinal cord or another structure and, in that way, protect and house that structure of the patient's body. The indentation also aims to limit an area where, if necessary, an incision can be made on said piece of mesh. Said indentation of the support element should be concave and directed towards the centre of the support element (ring) of the piece of mesh.

In a preferred embodiment of the invention, the support element is fixed to the piece of mesh so that the base of the indentation existing on the support element generally faces the narrower extremity of said piece of mesh.

In a preferred embodiment of the invention, the support element should be a filament (monofilament). It is possible, however, to foresee alternatives with more than one filament. Said support element should be made of either an absorbable or non-absorbable biasing (with memory) material, capable of being deformed and then resuming its previous shape, so as to maintain the piece of mesh stretched. In particularly preferred embodiment of the invention, the support element shall be made of extruded polydioxanone (PDO), polyglatin (e.g., VICRLY® sold by Ethicon, Inc.) or polyglycolic acid (e.g., DEXON® sold by US Surgical, Inc.). This list of materials should be understood as being non-limitative, since other materials (for example materials derived from collagen) may also be used provided they possess the above mentioned characteristics.

The diameter of the support element should be sufficient to ensure that the properties of resilience and elasticity. In a preferred embodiment, the diameter of the support element should up to 2.00 mm and, in an even more preferred embodiment, the diameter of the support element should be 1.20 mm.

In an alternative embodiment of the invention, there is a second piece of mesh. This second piece of mesh may or may not have a shape identical to the piece of mesh described above (hereinafter, the "first piece of mesh").

In a specific preferred embodiment of this alternative embodiment of the invention, said second piece of mesh will have an essentially ovoid shape which, when placed on said first piece of mesh, will be capable of partially accompanying the exterior border of the principal area of said first piece of mesh.

In another specific preferred embodiment, the second piece of mesh has a configuration similar to that of the support element only wider.

As in the case of the first piece of mesh, the second piece of mesh shall consist of a woven net made either of an absorbable or non-absorbable material.

The second piece of mesh is attached to said first piece of mesh, one on top of the other, so that the contours of the second piece of mesh essentially accompany the exterior border of the main surface area of said first piece of mesh shaped like a deformed water drop, thus creating an area of the prosthesis with two layers of mesh.

In this alternative embodiment, the support element is fixed (sandwiched) in between the first and second pieces of mesh. The support element may be fixed in any way that ensures its deformability with memory (elasticity) and does not harm the health of the patient. In a particularly preferred embodiment of the invention, the support element is sewn in between the first and second pieces of mesh using stitches of either an absorbable and/or non-absorbable monofilament material, such as polypropylene, (PFTE), amongst other materials available in the market.

The stitches are made along the inner and outer borders of all or part of the length of the support element. Preferably, the stitches are made using a specific programmable sewing machine that enables the sewing of the two pieces of mesh with great detail, thus ensuring that the three components (first and second pieces of mesh and the support element) form a unified whole that maintains the deformability with memory properties (i.e., elasticity).

The embodiments of the invention mentioned above are based on the concept of an implantable prosthesis that is essentially flat (plane). However, it is possible to design the prosthesis in different shapes and sizes so as to address more easily the correction of herninary defects, particularly in inguinal hernias. Consequently, the prosthesis of the present invention may be shaped so that it has a concave or convex shape or any other complex shape.

The major advantage of the implantable prosthesis of the present invention is that it does not require any grasping or fixing means to the body structures in the inguinal region. Indeed, in addition to the accommodation of the spermatic cord, which is not retained to or by any structure but is merely adjusted, there is no need for any sutures to maintain the prosthesis in the desired location (i.e. the present invention presents a truly tension-free solution). This does not mean that the surgeon can not employ some sutures with absorbable or non-absorbable threads or other fixing means should he so deem necessary.

The prosthesis of the present invention is the ideal medical device to complement the new surgical technique also invented by the inventors.

An additional advantage of the prosthesis of the present invention is the fact that it does not have a discontinuation (break) in the support element. By not having any discontinuation (break), it is possible to maintain the deformability and elasticity properties, whilst simultaneously avoiding the overlapping or folding of the support element's extremities in the section of the discontinuation (break).

Another advantage of the implantable prosthesis of the present invention is the fact that it does not require any reinforcements in any of its areas or sections, as is the case with many other prostheses of the prior art.

The implantable prosthesis of the present invention is suitable for inguinal hernias that manifest themselves in persons of both sexes, irrespectively of their classification, and is adequate for potential and existing defects in the inguinal floor.

BRIEF DESCRIPTION OF DRAWINGS

The present invention will be described below in more detail, by making reference to a preferred embodiment of the invention as shown in the attached drawings, said preferred embodiment being presented as an example and not to be interpreted as having any limitative effect on the scope of protection. Accordingly.

BEST MODE FOR CARRYING OUT THE INVENTION

By making reference to the drawings, a preferred embodiment of the invention will now be described below.

Figure 1:
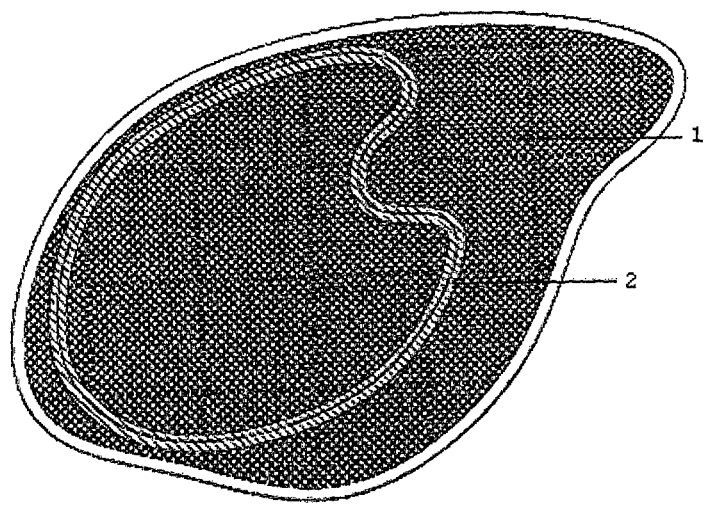
FIG. 1 shows an overall perspective view of an implantable prosthesis with the support element (2) fixed to the first piece of mesh (1)
Figure 2:
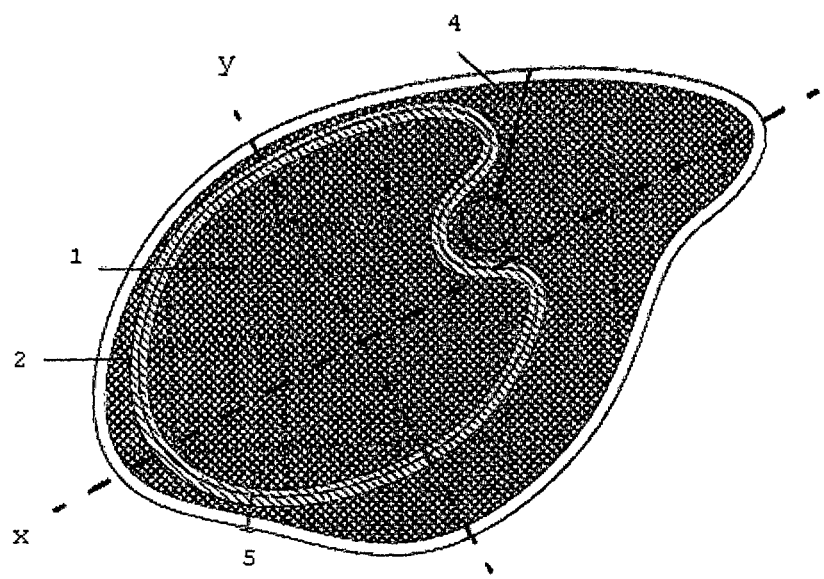
FIG. 2 shows an overall perspective view of the implantable prosthesis with the two pieces of mesh (1 and 3), where it is possible to see the major (x) and minor (y) axis, as well as the area that may be cut (4) when treating inguinal hernias in patients of the male sex.
Figure 3:
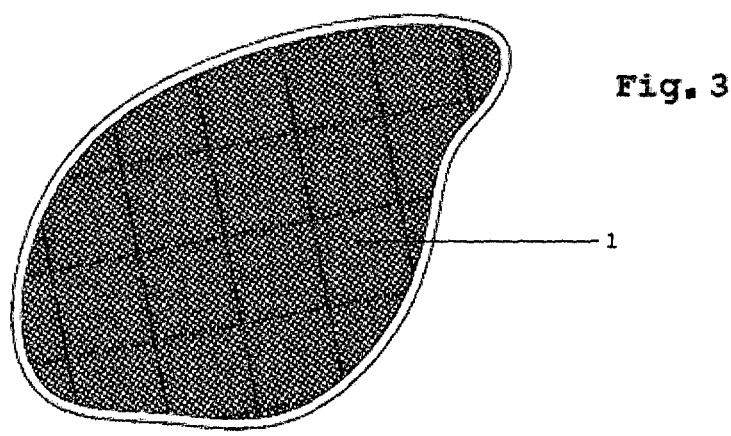
FIG. 3 shows a top view of the first piece of mesh (1)
Figure 4:
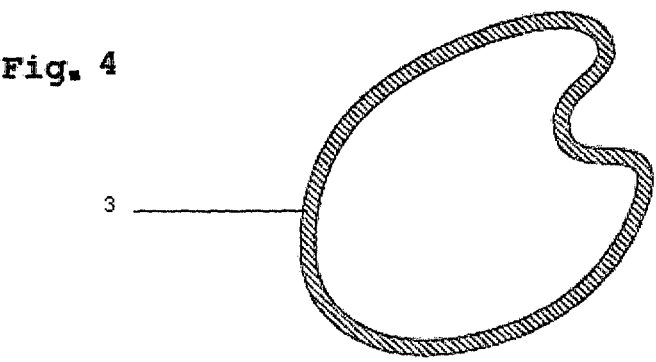
FIG. 4 shows a top view of the second piece of mesh (3)
Figure 5:
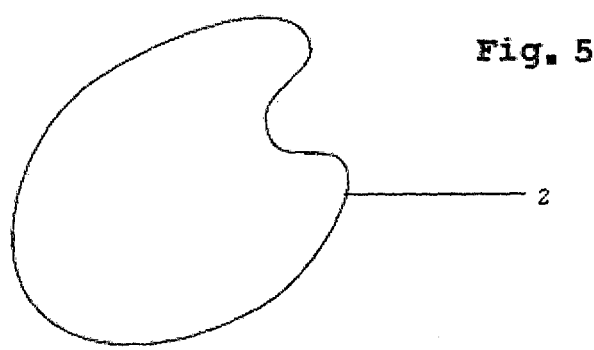
FIG. 5 shows a top view of the support element (2)
Figure 6:
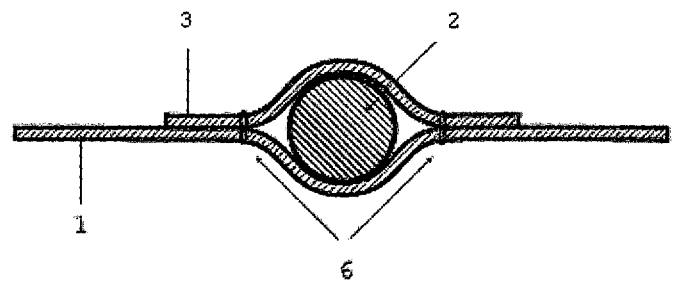
FIG. 6 shows a section view of area (5) of FIG. 2, illustrating the manner in which the second piece of mesh (3) is sewn to the first piece of mesh (1), with two continuous lines of stitching (6), one internal and the other external to the support element (2), so that said support element is free within the tunnel that is formed by the two pieces of mesh.
Figure 7:
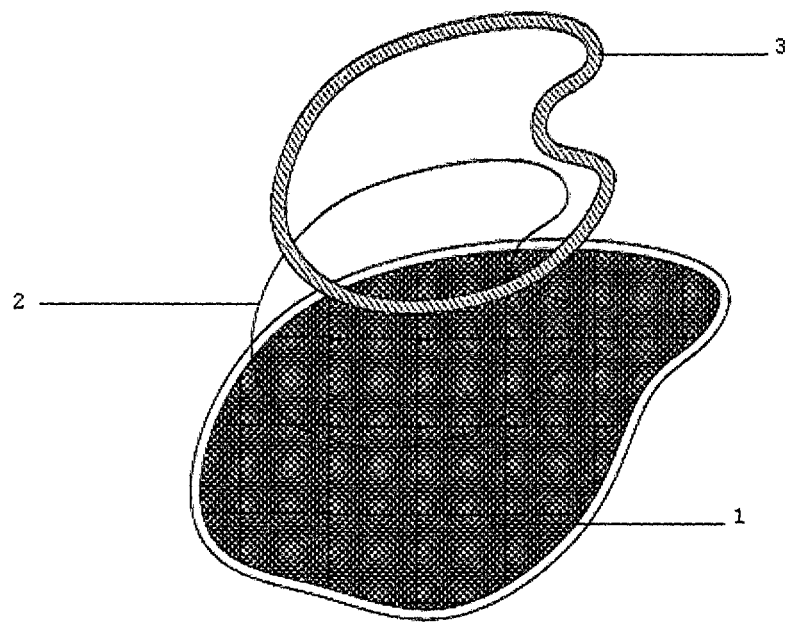
FIG. 7 shows a perspective view of the implantable prosthesis with all the components (1, 2 and 3) spatially separated although placed "in loco" in different planes.

As illustrated in FIG. 1, the implantable prosthesis comprises a first piece of mesh (1) connected to a support element (2) capable of providing properties of resilience/elasticity to said first piece of mesh (1).

The first piece of mesh (1) consists of a woven net made of a non-absorbable material. Said first piece of mesh (1) is shaped like a deformed water drop, asymmetric on its major (horizontal) or minor (vertical) axis, having one wider extremity and another opposite narrower extremity, with the main surface area of the first piece of mesh (1) having an essentially ellipsoid shape.

It is also foreseen that the first piece of mesh (1) have an axial cephalic extension. In addition to this, it is foreseen that first piece of mesh (1) also have another latero caudal extension.

The internal and external borders of said extremities have different convexities.

Making reference to FIG. 1, the lower extremity of the first piece of mesh (1) has an internal angle larger than the external angle of the opposite extremity. In other words, the lower (wider) extremity is generally obtuse and the top (narrower) extremity is acute.

The first piece of mesh (1) also has two slight indentations, one between the axial cephalic and latero caudal extensions and another medial in relation to the lower interior angle.

The first piece of mesh (1) is flat and capable of being inverted, so that it can be applied both on the right and left side of the patient.

The first piece of mesh (1) for an adult male shall have a length of 14.7 cm along its major (largest) axis and approximately 8.8 cm along its minor (shortest) axis. In embodiments for adult females or pelvises of smaller dimensions, the piece of mesh shall be 6.2 cm along its major (longest) axis and 9.7 cm along its minor (shortest) axis.

The support element (2) is shaped as a continuous ellipsoidal ring, with a concave indentation facing towards the centre of the ring.

When said ring is fixed to said first piece of mesh, the base of the indentation faces opposite to the narrower extremity of the first piece of mesh (1).

The support element (2) is preferably made from re-absorbable material (for example a monofilament of extruded polydioxanone), with a diameter of 1.20 mm.

Said indentation of the support element (2) seeks to limit an area (4) where, if necessary, an incision can be made in the first piece of mesh (1). There are no reinforcements of the prosthesis in any of its parts (and none are needed).

The support element (2) is fixed to the first piece of mesh (1) by means of a second piece of mesh (3).

The shape of the second piece of mesh (3) is similar to that of the support element (2) only flat and wider and, when placed over the first piece of mesh (1), follows partially the exterior contour of the first piece of mesh (1).

The second piece of mesh (3) may be made of the same material as the first piece of mesh (1) or of another absorbable or non absorbable material. The second piece of mesh (3) is sewn to the first piece of mesh (1), one on top of the other, with two continuous lines of stitching (6) in absorbable material, one external and the other internal in relation to the support element (2), thus enabling the support element (2) to remain free within a tunnel that is formed in between the two pieces of mesh (1 and 3).

It should be understood that the above description can incorporate various modifications of the parts that make up the prosthesis of the present invention which are presented merely as examples of possible embodiments and should not be considered as in any way limiting the scope of protection that is sought, the latter being defined solely by the claims of the present patent application.

The invention claimed is:

1. An implantable prosthesis for the repair of inguinal and femoral hernias, the implantable prosthesis comprising: at least one piece of mesh arranged to cover at least a portion of an inguinal or a femoral hernia, said at least one piece of mesh including a longest length along a first axis and a longest width along a second axis, wherein said longest length is longer than said longest width, wherein said first axis is perpendicular to said second axis, wherein said at least one piece of mesh includes a first extremity that is wider than an opposite extremity, at least one resilient, support element in the form of an uninterrupted ring attached to said at least one piece of mesh and surrounding a portion of said at least one piece of mesh, said at least one support element further comprising an indentation to receive a cord structure, said indentation directed towards the center of said ring along a direction of said first axis, wherein said at least one piece of mesh includes an extension extending away from said indentation along a direction of said first axis, said extension being free of said support element and forming said opposite extremity and wherein said at least one piece of mesh is asymmetric about said first axis and about said second axis.

2. The implantable prosthesis according to claim 1, characterized by said support element being an ellipsoid ring.

3. The implantable prosthesis according to claim 1, characterized by said support element being an ovoid ring.

4. The implantable prosthesis according to claim 1, characterized by said support element being a polygon with a number of sides equal or superior to six.

5. The implantable prosthesis according to claim 1, characterized by said at least one piece of mesh being shaped like a deformed water drop, whereby said at least one piece of mesh shaped like a deformed water drop having a main surface area that borders said first, wider extremity and has an essentially ellipsoid shape.

6. The implantable prosthesis according to claim 5, characterized by said first, wider extremity of said at least one piece of mesh having an internal angle larger than an external angle of said opposing extremity, and wherein an internal border of said opposing extremity and an external border of said first, wider extremity having different convexities.

7. The implantable prosthesis according to claim 5, characterized by said at least one piece of mesh further including a cephalic axial extension and a latero-caudal extension.

8. The implantable prosthesis according to claim 7, characterized by said at least one piece of mesh further including two slight indentations, one positioned between said cephalic axial extension and said latero-caudal extension and another medial in relation to said interior angle of said first, wider extremity.

9. The implantable prosthesis according to claim 1, characterized by said indentation of said support element being essentially concave.

10. The implantable prosthesis according to claim 5, wherein a base of said indentation opens to and faces said opposing extremity.

11. The implantable prosthesis according to claim 1, characterized by said support element being sandwiched between said at least one piece of mesh and a second piece of mesh.

12. The implantable prosthesis according to claim 11, characterized by either said at least one piece of mesh or said second piece of mesh being made of an absorbable material and the other of a non-absorbable material.

13. The implantable prosthesis according to claim 11, characterized by said second piece of mesh having a shape similar to that of said support element only wider.

14. The implantable prosthesis according to claim 11, characterized by said at least one piece of mesh being sewn to said second piece of mesh with continuous stitches of absorbable material, one external and the other internal in relation to said support element, said support element remaining free within a tunnel formed between said at least one piece of mesh and said second piece of mesh.

* * * * *